United States Patent
Sokolov et al.

(10) Patent No.: US 9,068,892 B2
(45) Date of Patent: Jun. 30, 2015

(54) METHOD FOR THE EMISSION ANALYSIS OF THE ELEMENTAL COMPOSITION OF LIQUID MEDIA

(71) Applicant: Research and Production Enterprise "Bourevestnik", St. Petersburg (RU)

(72) Inventors: Michail Andreyevich Sokolov, St. Petersburg (RU); Vladimir Iosifovich Tsvetkov, St. Petersburg (RU); Oxana Yurievna Anufrieva, St. Petersburg (RU)

(73) Assignee: Research and Production Enterprise "Bourevestnik", St. Petersburg (RU)

( * ) Notice: Subject to any disclaimer, the term of this patent is extended or adjusted under 35 U.S.C. 154(b) by 0 days.

(21) Appl. No.: 14/127,268

(22) PCT Filed: Dec. 26, 2012

(86) PCT No.: PCT/RU2012/001118
§ 371 (c)(1),
(2) Date: Dec. 18, 2013

(87) PCT Pub. No.: WO2013/105879
PCT Pub. Date: Jul. 18, 2013

(65) Prior Publication Data
US 2014/0313508 A1    Oct. 23, 2014

(30) Foreign Application Priority Data
Jan. 12, 2012 (RU) .................. 2012101985

(51) Int. Cl.
*G01J 3/30* (2006.01)
*G01J 3/443* (2006.01)
*G01N 21/67* (2006.01)
*G01N 33/18* (2006.01)

(52) U.S. Cl.
CPC ................. *G01J 3/443* (2013.01); *G01N 21/67* (2013.01); *G01N 33/18* (2013.01)

(58) Field of Classification Search
USPC .................................................. 356/300–334
See application file for complete search history.

(56) References Cited

U.S. PATENT DOCUMENTS

2006/0118782 A1* 6/2006 Zettl et al. ....................... 257/40

* cited by examiner

*Primary Examiner* — Abdullahi Nur
(74) *Attorney, Agent, or Firm* — Garcia-Zamor IP Law; Ruy M. Garcia-Zamor

(57) ABSTRACT

The proposed method is related to the field of physics and atomic emission spectrometry analysis. This atomic emission analysis method includes initiation of a local electric discharge in the liquid under analysis with the formation of a current-carrying channel in the volume of a diaphragm opening made in a member of the electrolytic cell structure, and detection of the generated emission spectra of the chemical elements being determined. The elements being determined are first deposited in the current-conducting channel volume at current insufficient for initiating a local electric discharge, then the current direction is changed and its intensity is increased for initiating a local electric discharge, and emission generated in the liquid being analyzed is detected as emission spectra of the elements being determined. The deposition current intensity can be selected according to elements to be determined and their concentration in the liquid.

2 Claims, 3 Drawing Sheets a)

b)

METHOD FOR THE EMISSION ANALYSIS OF THE ELEMENTAL COMPOSITION OF LIQUID MEDIA

FIELD OF THE INVENTION

The invention is related to the field of technical physics, in particular, to spectral methods for determining elemental composition of liquid media using an electric discharge in the liquid as a source of spectra. The method can be used for determining elemental composition of liquid media. The areas of application include water treatment systems at public water supply facilities, nuclear and thermal power industries, chemical industry, food industry processes (for water quality control), environment monitoring, etc.

CROSS REFERENCE TO RELATED APPLICATIONS

This application claims priority to the following patent applications: (1) Patent Cooperation Treaty Application PCT/RU2012/001118 filed Dec. 26, 2012; the of the above cited application is hereby incorporated by reference herein as if fully set forth in its entirety.

BACKGROUND OF THE INVENTION

One of the main characteristics providing the possibility of use of atomic emission spectral (AES) analysis for solution of particular analytical problems is sensitivity (detection limit) defined by intensity of AES lines of impurity atoms in the specimen (sample) being analyzed.

At present, primarily atomic-emission and atomic-absorption spectroscopy methods are used for determining the impurities concentration in liquid media with detection limit of lower than 1 ppm [Journal of Analytical Chemistry. 2011, vol. 66, No. 9, pp. 900-915]. To determine the concentration of impurities with the use of analytical instruments implementing such methods, one must perform sampling, feed appropriate amount of inert or combustible gas in the course of each analysis, and provide power supply, generally higher than 1 kW. The use of such analyzers requires provision of certain conditions, availability of highly skilled operating personnel and material expenses, which complicates the application of such methods in mobile and self-contained versions.

There is a prior art method of emission analysis based on an electric discharge directly in the liquid being analyzed (EDBC i.e. electric discharge corresponding to the boiling in a channel). [B. Zuyev, V. Yagov, M. Getsina, B. Rudenko, Journal of Analytical Chemistry, 2002, vol. 57, No. 10, pp. 1072-1077]. The method uses for EDBC initiation a two-electrode electrolytic cell filled with electrolyte solution and having spaces separated by a dielectric partition (membrane). The membrane has an opening with a diameter of about 1 mm and a length equal to the membrane thickness, which forms a channel for liquid passing between two spaces of the cell. High-voltage electrodes are arranged on different sides of the membrane. Voltage of (1.2-2.8) kV, depending on the composition of the analyzed solution and on the channel size, is applied to the cell electrodes. As a high-voltage electric circuit is closed in the channel where current density is much higher than in the rest part of the vessel, the liquid boils due to ohmic heat generation, and a steam bubble is formed. Then the channel is blocked by the steam plug, and a gas discharge accompanied by light emission arises between the plug walls. Optical emission intensity of atoms in the EDBC torch serves as an analytical signal for further recording of the emission spectra by means of a spectrometer.

The drawback of the above-described method is that the emission spectra intensity detected for the majority of elements, including alkaline-earth metals, is low, significantly lower than for alkaline metals (according to the inventors' data, the detection limit was 0.05 ppm for sodium, 1.5 ppm for calcium and 5 ppm for magnesium).

The prior art method most similar to the proposed invention is a method for emission analysis of elemental composition of liquid media based on local electric discharge (LED) in liquid [Patent RU 2368895, G01N 27/62, 27.09.2009]. The method also includes electric current flow through the liquid under analysis by means of electrodes separated by a partition (membrane) made of dielectric material and having a diaphragm opening therein. To initiate a local electric discharge (LED) in the diaphragm opening, concentration of electric power dispersed in a unit of the liquid volume sufficient for obtaining and sustaining a stable discharge is provided in the diaphragm opening where a current-carrying channel is formed. This takes place due to smaller volume of liquid participating in the discharge (diameter of the diaphragm channel is 0.1 mm) and higher discharge voltage (up to 15 kV). One of the electrodes (a current-carrying member) is located near the diaphragm opening, directly in the area of the discharge. LED is initiated after polarization of the above-mentioned electrode by current of the same polarity as that of LED current. The polarization current intensity is lower than that required for LED inception but sufficient for efficient mass transfer between this electrode and ions of the liquid being analyzed (in practice, 0.1-0.3 of LED current). Emission spectra of elements contained in the liquid excited by LED are recorded by means of a spectrometer.

The drawbacks of the method include presence of emission lines of the electrode material in the recorded spectrum of analyzed liquid and spatial instability of emission detected by the spectrometer due to the discharge movement over the electrode surface. Both drawbacks are caused by the electrode location in the area of the discharge, which leads to gradual destruction (sputtering). This results in instability of the detected spectra and, therefore, adversely impacts reproducibility of the measurement results and long-term operation reliability of the device.

DISCLOSURE OF THE INVENTION

The technical result of the proposed method for emission analysis of elemental composition of liquid media is higher stability and reproducibility of measurement results and better long-term operation reliability of the device.

The technical result is obtained by the proposed method for emission analysis of elemental composition of liquid media including initiation of a local electric discharge in the liquid under analysis with the formation of a current-carrying channel in the volume of a diaphragm opening made in a member of the electrolytic cell structure, and detection of the generated emission spectra of the chemical elements being determined, wherein the elements being determined are first deposited in the current-conducting channel at current insufficient for initiating a local electric discharge, then the current direction is changed and its intensity is increased for the purpose of initiating a local electric discharge, and then emission generated in the liquid being analyzed is detected as emission spectra of the elements being determined.

The method according to the invention differs from the prior art method in that the elements being determined are first deposited in the current-conducting channel volume at current insufficient for initiating a local electric discharge, then the current direction is changed and its intensity is increased in order to initiate a local electric discharge, and emission generated in the liquid being analyzed is detected as emission spectra of the elements being determined.

The deposition current intensity can be selected according to elements to be determined and their concentration in the liquid.

The combination of distinguishing features and their interrelation with restrictive features in the proposed invention provides higher stability and reproducibility of the measurement results and better long-term operation reliability of the device.

INDUSTRIAL APPLICABILITY

According to the invented method, emission analysis of elemental composition of liquid is performed as follows. Volume of the electrolytic cell is filled with the liquid to be analyzed, the cell having in one of its structural members a diaphragm opening of small cross-sectional area and small length, which forms a diaphragm channel. The volume of the electrolytic cell is further comprised of two reservoirs which are disposed one either side of the diaphragm channel to ensure that the liquid to be analyzed fully fills the diaphragm channel, such that an electrolytic cell structure with a first reservoir and a second reservoir are configured to hold the liquid to be analyzed. Elements to be determined are deposited in the formed current-conducting channel by way of provision of current between the cell electrodes mounted on different sides of the diaphragm opening. The current intensity during deposition is insufficient for initiation of LED. In other words, an initial current in the current carrying channel is provided such that at least some of the elements in the liquid are deposited within the current carrying channel, the initial current being insufficient to create atomization. Upon completion of the deposition process, LED is initiated in the diaphragm channel; for this purpose, current direction is changed and current intensity is increased. The process may occur in such a way that atomizing of at least the elements or the elements and the liquid occurs. The electrolytic cell structure is configures such that atomization of matter in the current carrying channel in the diaphragm is mass transfer neutral with regard to an allocation of liquid between the first and second reservoirs within the electrolytic cell structure. The light emission generated during LED is detected by a spectrometer as an analytical signal for producing emission spectra of the chemical elements being determined Deposition current intensity is selected according to elements to be determined and their concentrations in the liquid being analyzed. For one and the same set of elements being determined, the lower are their concentrations the longer is the time required for deposition.

Figure 1:
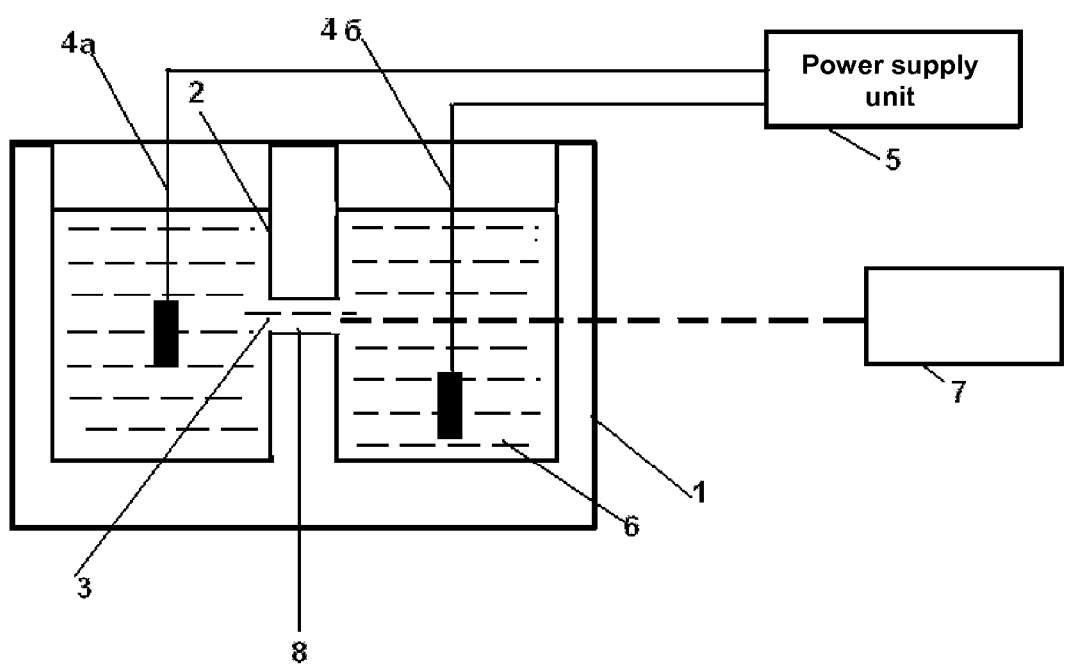
FIG. 1 shows diagrammatically a version of a device for implementation of the method according to the invention.

Feasibility of practical implementation and efficiency of the proposed method for emission analysis of elemental composition of liquid media is confirmed by operation of the device, a version of which is shown diagrammatically on FIG. 1. In accordance with the version of the device design shown on FIG. 1, a prototype unit was made and used for testing the proposed method, which confirms not only practicability but also industrial applicability of this engineering solution.

The device for implementation of the proposed method shown on FIG. 1 comprises body 1 with dielectric partition 2 dividing internal volume of the body and having diaphragm opening 3. Electrodes 4a and 4b are mounted on different sides of the partition 2; they are connected to stabilized high voltage source 5. The body 1 is filled with electrolytic liquid 6 elemental composition of which is to be analyzed. Spectrometer 7 is installed outside the body 1 so as to be able to detect light emission generated in LED zone 8.

In prototype units of the device (FIG. 1), walls of the body 1 and partition 2 are made of quartz glass. Thickness of the partition 2 is between 0.2 mm and 1.5 mm. The area of the diaphragm opening 3 is determined based on the value of voltage at electrodes 4a and 4b, thermal conductivity and electric conductivity of liquid 6 and thickness of dielectric partition 2. Diameter of the diaphragm opening 3 was from 0.1 mm to 0.05 mm, that is, volume of the diaphragm channel was less than 0.1 mm.sup.3. The high voltage source 5 provided voltage adjustment from 0 to 10 kV and was connected through a ballast resistance of 20 kOhm or more for stabilization. The electrodes 4a and 4b were made of corrosion resistant material, in particular, of titanium with ruthenium oxide coating. A quartz fibre-optic lead mounted in LED zone 8 was used for the sampling of the detected emission.

The device (FIG. 1) operates as follows. The high voltage from source 5 applied to electrodes 4a and 4b located in the body 1 filled with the liquid 6 being analyzed produces electric current between the electrodes, which forms a current-carrying channel in the volume of the diaphragm opening 3. Intensity of the current shall be sufficient to ensure efficient mass transfer of impurities present in the liquid 6 being analyzed to the channel, and the as higher sensitivity of analysis is required (i.e., the lower is concentration of elements to be determined in the liquid under analysis), as longer time of the current action should be selected. In practice, relative magnitude of the current is 0.05 to 0.3 of LED current magnitude, and the time of its action is about 30-500 s. During the current action, elements to be determined are deposited in the current-carrying channel 3. Upon completion of deposition, LED is initiated. For LED initiation, polarity of electrodes 4a, 4b is changed, and voltage applied to the electrodes is increased. To ensure stable LED in the liquid, voltage within the range from 5 kV to 15 kV is required while the partition 2 thickness should be from 0.2 mm to 1.5 mm and diameter of the diaphragm opening 3—from 0.1 mm to 0.05 mm. The discharge, being localized in small volume of liquid in the dielectric partition 2 channel 3, creates high concentration of power—sufficient for ionization or atomization of the liquid and deposited elements to be determined. The ionization or atomization of the liquid is mass transfer neutral with regards to the two reservoirs disposed on either side of the dielectric partition and current carrying channel. The light emission generated during this process is recorded in zone 8 by a spectrometer 7, as an analytical signal for producing emission spectra of the elements being determined It should be noted that the voltage corresponding to LED inception (ignition) depends also on conductivity of the liquid being analyzed. For example, for KCl solution with concentration from 0.0001 M to 0.1 M, LED inception voltage varied from 3 kV to 10 kV. In this case, voltage drop in the current-carrying channel was from 0.5 kV to 2 kV, and current intensity was from 0.02 A to 0.1 A.

The high voltage supply is provided by high-voltage source 5, stabilization of the source current being one of the prerequisites of LED stability. Despite a high temperature, long-term stable operation of diaphragm opening 3 in the LED zone is provided due to intense heat abstraction by liquid 6.

PREFERRED IMPLEMENTATION OF THE INVENTION

Figure 2:
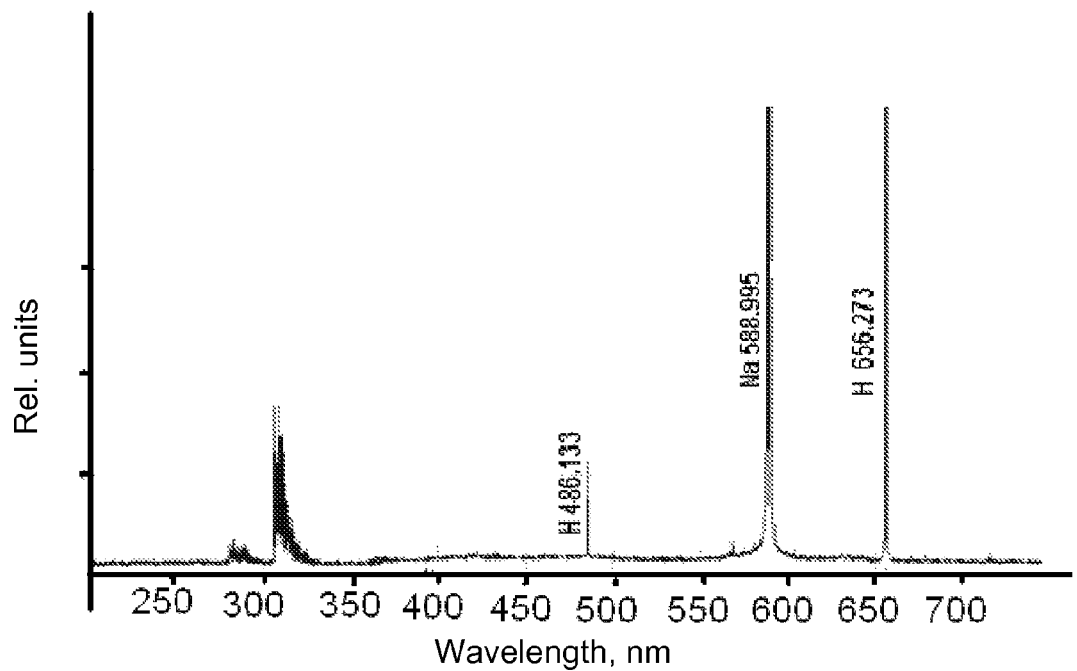
FIG. 2 shows tap water spectra obtained:
a—using a local electric discharge as a source;
b—by the method according to the invention.
Figure 2:
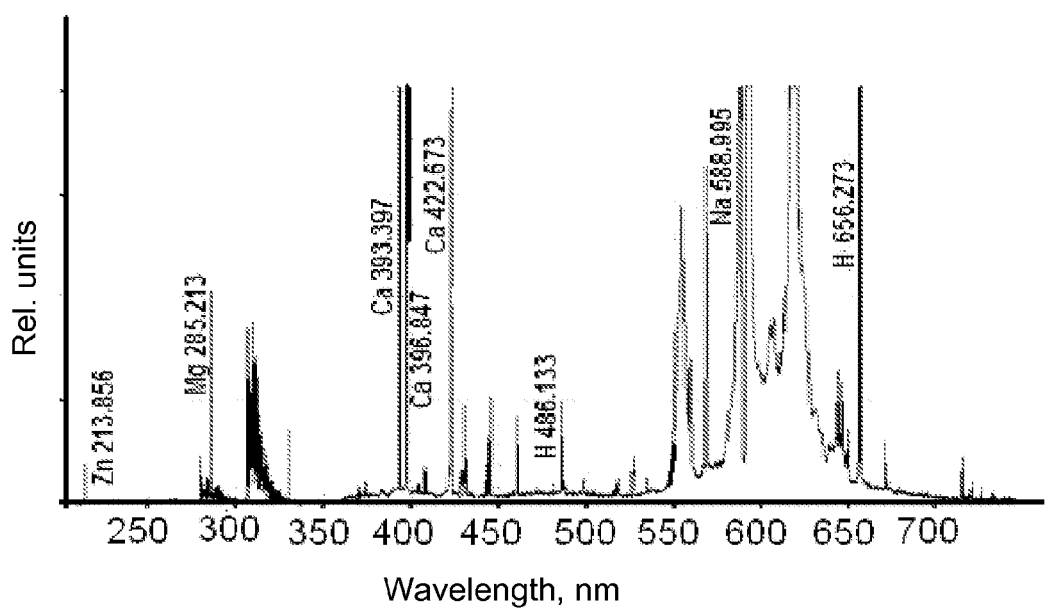
Figure 3:
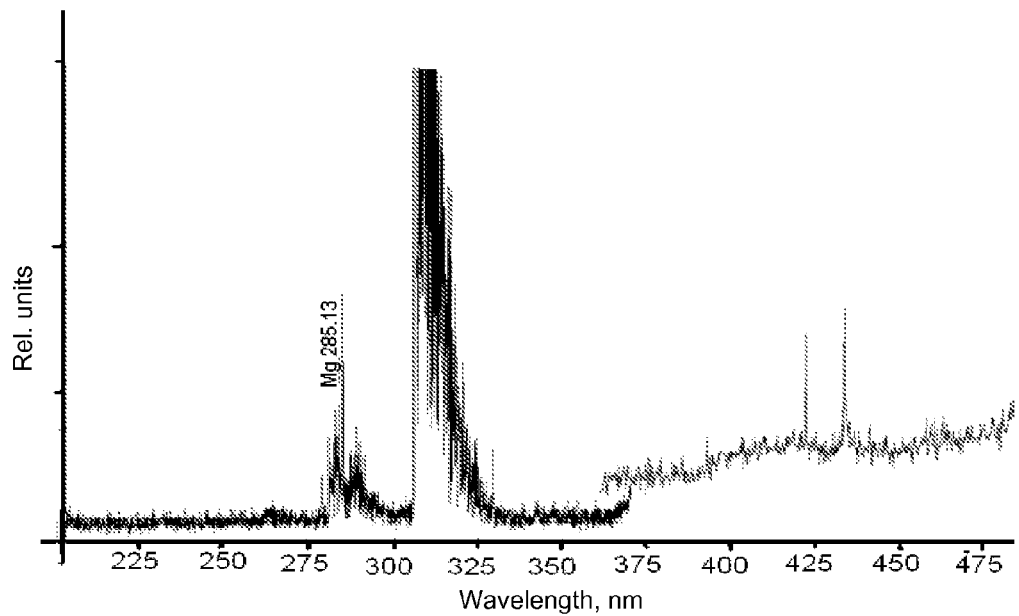
FIG. 3 shows spectra of the model solution containing 0.01 ppm of lead, copper, zinc and cadmium each, and 1 ppm of calcium obtained:
a—using a local electric discharge as a source;
b—by the method according to the invention.
Figure 3:
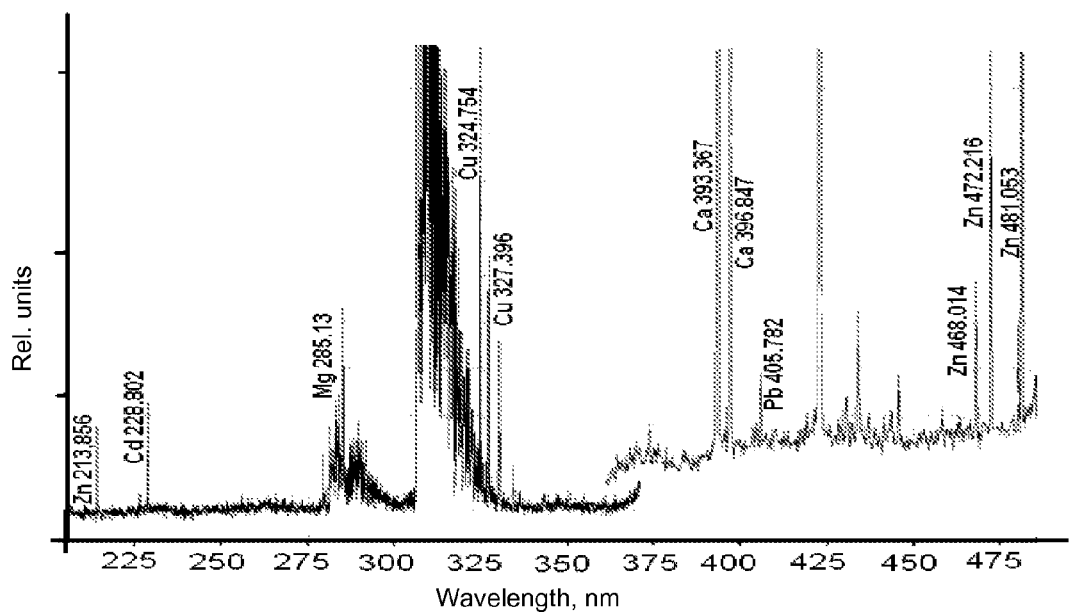

The results of tests of the proposed emission analysis method performed using the device (FIG. 1) and respective emission spectra recorded by spectrometer 7 are presented on FIG. 2 and FIG. 3.

The tap water spectrum (FIG. 2*a*) was obtained with direct LED initiation without deposition of the elements to be determined The tap water spectrum (FIG. 2*b*) was obtained in accordance with the method proposed, i.e., with prior deposition of the elements to be determined (during 150 s) and subsequent LED initiation. The spectrum (FIG. 2*b*) reflects reliably emission lines of alkaline (Na .lamda. 588.995 nm), alkaline-earth (Ca .lamda. 393.397 nm, Ca .lamda. 396.847 nm, Ca .lamda. 422.673 nm, Mg .lamda. 285.213 nm) and other (Zn .lamda. 468.014 nm, Zn .lamda. 472.216 nm, Zn .lamda. 481.053 nm) metals, while the spectrum (FIG. 2*a*) shows alkaline metal lines only (Na .lamda. 588.995 nm).

The spectra of model solution (FIG. 3) containing 0.01 mg/L of lead, 0.01 mg/L of copper, 0.01 mg/L zinc and 1 mg/L calcium were obtained using the device (FIG. 1) under the same conditions as for the spectra on FIG. 2: the spectrum on FIG. 3*a* was obtained with direct LED initiation and the spectrum on FIG. 3*b* was obtained by the method according to the invention. The spectrum of the model solution with a concentration level of 0.01 ppm (FIG. 3*b*) obtained by the method according to the invention reflects reliably emission lines of lead (Pb .lamda. 405.782 nm), copper (Cu .lamda. 324.754 nm, Cu .lamda. 327.396 nm) and zinc (Zn .lamda. 468.014 nm, Zn .lamda. 472.216 nm, Zn .lamda. 481.053 nm), cadmium (Cd .lamda. 228.802 nm) as well as calcium (Ca .lamda. 393.397 nm, Ca .lamda. 396.847 nm) and cadmium (Cd .lamda. 228.802 nm) while these lines are not identified in the spectrum shown on FIG. 3*a*.

Comparison of the shown spectra demonstrates that only combination and proper sequence of all of the operations included in the proposed method leads to achievement of the claimed result, i.e., higher stability and reproducibility of measurement results. Reliability of long-term operation of the device is ensured by the use of corrosion resistant material for the device body and also by the absence of any electrically conductive destructible members in the LED zone. Higher intensity of spectral lines of a wide range of elements detected by the method according to the invention makes it possible to determine elements contained in the liquid under analysis in rather low concentrations.

The invention claimed is:

1. A method for determining a composition of liquid having elements therein, comprising:

providing an electrolytic cell structure with a first reservoir and a second reservoir configured to hold the liquid to be analyzed, a current-carrying channel formed in a diaphragm separating the first reservoir and the second reservoir such that the current carrying channel connects and establishes liquid communication between the first reservoir and the second reservoir, providing liquid in the first reservoir and the second reservoir such that liquid is present in the current carrying channel, establishing an initial current in the current carrying channel such that at least some of the elements in the liquid are deposited within the current carrying channel, the initial current being insufficient to create atomization, atomizing of at least one of the group of (1) the at least some elements present in the current-carrying channel and (2) the at least some of the elements and the liquid present in the current-carrying channel, the atomizing being performed by reversing the polarity of the initial current and by increasing intensity of the initial current within the current carrying channel to create a local electric discharge, wherein the electrolytic cell structure is configured such that atomization of matter in the current carrying channel in the diaphragm is mass transfer neutral with regard to an allocation of liquid between the first and second reservoirs within the electrolytic cell structure, and detecting an emission generated by the local electric discharge in the current carrying channel;

analyzing the emission to determine the composition of the at least some elements.

2. The Method for emission analysis according to claim 1, wherein the initial current intensity is selected in accordance with elements to be determined and their concentrations in the liquid.

* * * * *